(12) United States Patent
Ichikawa et al.

(10) Patent No.: US 9,518,224 B2
(45) Date of Patent: Dec. 13, 2016

(54) ORGANIC SEMICONDUCTOR PARTICULATE MATERIAL, ORGANIC SEMICONDUCTOR THIN-FILM, DISPERSION LIQUID FOR FORMING ORGANIC SEMICONDUCTOR FILM, METHOD FOR PRODUCING ORGANIC SEMICONDUCTOR THIN-FILM, AND ORGANIC THIN-FILM TRANSISTOR

(75) Inventors: Musubu Ichikawa, Nagano (JP); Hyeon-Gu Jeon, Nagano (JP); Naomi Oguma, Tokyo (JP); Naoki Hirata, Tokyo (JP); Hisao Kono, Tokyo (JP)

(73) Assignees: Shinshu University, Nagano (JP); Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 13/819,636

(22) PCT Filed: Aug. 17, 2011

(86) PCT No.: PCT/JP2011/068623
§ 371 (c)(1),
(2), (4) Date: Feb. 27, 2013

(87) PCT Pub. No.: WO2012/029544
PCT Pub. Date: Mar. 8, 2012

(65) Prior Publication Data
US 2013/0153884 A1 Jun. 20, 2013

(30) Foreign Application Priority Data
Aug. 29, 2010 (JP) .................. 2010-191604

(51) Int. Cl.
H01L 51/00 (2006.01)
C09K 19/34 (2006.01)
C07D 471/04 (2006.01)
C09B 5/62 (2006.01)
H01L 51/05 (2006.01)

(52) U.S. Cl.
CPC ......... *C09K 19/3483* (2013.01); *C07D 471/04* (2013.01); *C09B 5/62* (2013.01);
(Continued)

(58) Field of Classification Search
CPC .................................................. H01L 51/0067
(Continued)

(56) References Cited

U.S. PATENT DOCUMENTS

| 7,198,977 B2 | 4/2007 | Shukla et al. |
| 7,326,956 B2 | 2/2008 | Shukla et al. |
| 2009/0250676 A1 | 10/2009 | Haramoto |

FOREIGN PATENT DOCUMENTS

| JP | 2004-335932 | 11/2004 |
| JP | 2005-281180 | 10/2005 |

(Continued)

OTHER PUBLICATIONS

Minoru English Translation from EPO web site (http://worldwide.espacenet.com).*

(Continued)

*Primary Examiner* — Peniel Gumedzoe
*Assistant Examiner* — Christopher Johnson
(74) *Attorney, Agent, or Firm* — Hamre, Schumann, Mueller & Larson, P.C.

(57) ABSTRACT

Provided are a fine-particulate organic semiconductor material, a thin organic semiconductor film and an organic transistor. The fine-particulate organic semiconductor material is in a form of fine particles and is usable as an organic semiconductor material. The fine particles are fine thermotropic liquid crystal particles that undergo a phase transition into a liquid crystal state when heated to a temperature of from 50° C. to 350° C. The fine-particulate organic semiconductor material can easily and uniformly form the thin organic semiconductor film over a large area by a film (Continued)

printing process or a dispersion coating process. The thin organic semiconductor film has high electron mobility and high ON/OFF value.

5 Claims, 5 Drawing Sheets

(52) U.S. Cl.
CPC ...... *C09K 19/3488* (2013.01); *H01L 51/0053* (2013.01); *H01L 51/0076* (2013.01); *H01L 51/0562* (2013.01); *Y10T 428/2982* (2015.01)

(58) Field of Classification Search
USPC .......................................................... 257/40
See application file for complete search history.

(56) References Cited

FOREIGN PATENT DOCUMENTS

| JP | 2008-524846 | 7/2008 |
|---|---|---|
| JP | 2008-524869 | 7/2008 |
| JP | 2009-200484 | 9/2009 |
| JP | 2009-218369 | 9/2009 |
| KR | 2008-0042821 | 5/2008 |

OTHER PUBLICATIONS

Yang et al., "Solvent effect on the self-assembled structure of an amphiphilic perylene diimide derivative," J. Phys. Chem. B 2008, 112, 7196-7202.*

Chesterfield et al.: "Organic Thin Film Transistors Based on N-Alkyl Perylene Diimides: Charge Transport Kinetics as a Function of Gate Voltage and Temperature"; J. Phys. Chem. B 2004, 108, pp. 19281-19292.

Tatemichi et al.: "High mobility n-type thin-film transistors based on N, N'-ditridecyl perylene diimide with thermal treatments"; Applied Physics Letters 89, 112108 (2006), 3 pages.

Strujik et al.: "Liquid Crystalline Perylene Diimides: Architecture and Charge Carrier Mobilities"; J. Am. Chem. Soc. 2000, 122, pp. 11057-11066.

* cited by examiner

ORGANIC SEMICONDUCTOR PARTICULATE MATERIAL, ORGANIC SEMICONDUCTOR THIN-FILM, DISPERSION LIQUID FOR FORMING ORGANIC SEMICONDUCTOR FILM, METHOD FOR PRODUCING ORGANIC SEMICONDUCTOR THIN-FILM, AND ORGANIC THIN-FILM TRANSISTOR

TECHNICAL FIELD

This invention relates to a thermotropic liquid crystal material, which is in the form of fine particles, is usable as an organic semiconductor material and, when heated to a temperature of from 50° C. to 350° C., undergoes a phase transition into a liquid crystal state. The present invention also relates to a thin organic semiconductor film formed with the fine particulate material, a dispersion containing the fine particulate material dispersed therein and useful in forming an organic semiconductor film, a process for producing the thin organic semiconductor film with the dispersion, and an organic thin-film transistor making use of the thin organic semiconductor film.

BACKGROUND ART

The progress of a high-level information-oriented society in recent years is remarkable, and the development of digital technologies has led to the penetration of computers and communication technologies such as computer networks in everyday life. Keeping in step with this penetration, flat-screen TV sets and notebook-size personal computers have become increasingly popular, resulting in an increasing demand for displays such as liquid crystal displays, organic EL displays and electronic paper displays. Especially in recent years, there is an outstanding move toward larger displays of higher definition, leading to an ever increasing number of pixels. It is, therefore, necessary to assemble numerous field-effect transistors corresponding to the number of pixels. In a liquid crystal display, the liquid crystal is driven by providing the respective pixels with field-effect transistors as active elements and performing ON/OFF control of signals.

As field-effect transistors for use as active elements, thin-film transistors can be used. The performance of the thin-film transistors is determined by the semiconductor material and structure employed therein. In their performance, the availability of particularly high carrier mobility and high ON/OFF ratio makes it possible to obtain a large current, thereby enabling not only to drive an organic EL device or the like but also to miniaturize the thin-film transistors and to provide an improved contrast.

For thin-film transistors useful as active elements, a silicon-based semiconductor material such as amorphous silicon or polysilicon can be used as an inorganic semiconductor material. In this case, a thin-film transistor is fabricated by forming such a silicon-based semiconductor material in a multilayered structure such that source, drain and gate electrodes are successively formed on a substrate.

For the fabrication of thin-film transistors making use of the above-described silicon-based semiconductor material, however, large-scale and costly fabrication facilities are needed, and because of the use of photolithography, many process steps have to be gone through, resulting in a practical problem that the fabrication cost becomes higher. Furthermore, the fabrication requires high temperatures of from 300° C. to 500° C. or even higher, which lead not only to still higher fabrication cost but also to a problem that inorganic semiconductor layers can be hardly formed on plastic substrates or flexible plastic films.

On the other hand, organic thin-film transistors, which make use of thin organic semiconductor films comprised of an organic semiconductor material, are fabricated by a vapor deposition process (vacuum film-forming process) or a solution coating process (film printing process), and have the possibility of lower cost, larger area and lighter weight. Further, thin organic semiconductor films can be formed at a lower temperature compared with inorganic semiconductor layers, and therefore, can achieve cost reduction in this respect. In addition, such thin organic semiconductor films can be formed on plastic substrates or flexible plastic films, and therefore, can achieve weight reduction, and therefore, they can also be applied to flexible electronic devices and the like.

For the above-described merits, many organic semiconductor materials have been studied to date, and those making use of low-molecular compounds or conjugated high-molecular compounds as thin organic semiconductor films are known. Nonetheless, the conjugated high-molecular compounds are not considered to be fully satisfactory in performance when formed into organic thin-film transistors, although they have excellent solubility in solvents and enable to form thin organic semiconductor films by a simple solution coating process. The low-molecular compounds, on the other hand, exhibit high performance as organic thin-film transistors, but are accompanied by a problem in that they have poor solubility in solvents and can be hardly formed into thin films. As a method for producing a thin organic semiconductor film, the formation of the thin semiconductor film by a vapor deposition process or the formation of the thin organic semiconductor film by a solution coating process, which makes use of a dilute solution, can be mentioned. It would be very convenient if it would be possible to form a thin organic semiconductor film especially by the simple solution coating process out of these two processes. However, the solution coating process involves a problem in that, because a thin film is formed with a dilute solution of such a compound as dissolved in a solvent, it is difficult to stably obtain a film thickness sufficient to obtain stable performance as an organic transistor. An organic semiconductor material of high solubility is desired accordingly. However, high solubility and high performance are in a trade-off relationship, and a material for thin semiconductor films, said material being equipped with both high solubility and high performance, has not been developed yet.

Semiconductor materials include n-type semiconductor materials for obtaining n-type semiconductors and p-type semiconductor materials for obtaining p-type semiconductors, and for the reasons to be mentioned below, there is a long-awaited desire for the development of materials capable of exhibiting high performance especially as n-type semiconductor materials. In an n-type semiconductor material, electrons move as main carriers to produce an electric current. In a p-type semiconductor material, on the other hand, holes move as main carriers to produce an electric current. Pentacene materials and thiophene materials, which are known as organic semiconductor materials that exhibit high performance, are semiconductor materials that exhibit p-type characteristics. However, reports on n-type organic semiconductor materials of high performance are limited. For further developments of organic electronics, lower power consumption, simpler circuits and the like are essential, and therefore, organic complementary MOS circuits which require both n-type and p-type organic semiconductor materials, such as complementary metal-oxide semiconductors (CMOS), are needed. There is, accordingly, an ever-increasing desire for n-type organic semiconductor materials of high performance.

As n-type organic semiconductor materials, naphthalene imide, naphthalene diimide, and derivatives thereof are known to date. However, none of these n-type organic semiconductor materials have been reported to have high performance as thin-film transistors.

On the other hand, Non-patent Document 1 describes a low-molecular compound having the perylene skeleton and an electron mobility of 0.6 $cm^2/Vs$, and makes mention about the possibility that its use in an organic thin-film transistor makes it possible to exhibit high performance (Non-patent Document 1).

As to organic thin-film transistors making use of perylene tetracarboxylic acid derivatives, there are those to be described below. Patent Document 1 describes that a thin film transistor comprised of an organic semiconductor material, which contains a perylene tetracarboxylic diimide derivative having a carbocyclic or heterocyclic aromatic ring system substituted with fluorine-containing groups, has a mobility of from 0.05 to 0.2 $cm^2/Vs$ and an ON/OFF ratio of from $10^4$ to $10^5$ and exhibits stability in air and excellent reproducibility. Patent Document 2 describes that a thin film transistor comprised of an organic semiconductor material layer, which contains a perylene tetracarboxylic diimide derivative having substituted or unsubstituted phenylalkyl groups, has a mobility of from 0.04 to 0.7 $cm^2/Vs$ and an ON/OFF ratio of from $10^4$ to $10^5$ and exhibits stability in air and excellent reproducibility.

Thin organic semiconductor films formed by a process such as the above-mentioned vacuum film-forming process or film printing process (solution coating process) generally have a polycrystalline structure formed of minute crystals aggregated together. Such thin organic semiconductor films contain numerous grain boundaries and defects. These crystal grain boundaries and defects act as a cause of inhibition of the transport of charges. The vacuum film-forming process and film printing process are, therefore, difficult to uniformly form a thin organic semiconductor film over a large area. These processes have hence been practically difficult to fabricate organic semiconductor devices having stable device performance.

To overcome such problems, the present inventors have already made a proposal as will be described below. Described specifically, the present inventors have proposed an organic thin-film transistor, which makes use of a thin organic semiconductor film produced by a vacuum film-forming process from N,N'-ditridecyl-3,4,9,10-pelylene dicarboxylic acid imide, an organic semiconductor material having a thermotropic liquid crystal phase at and below its decomposition temperature, and subjected to heat treatment in a temperature range in which the organic semiconductor material presents a smectic liquid crystal phase (Non-patent Document 2: 2.1 $cm^2/Vs$ electron mobility). The present inventors have then proceeded with a further study on the solubilization of perylene compounds to form thin organic semiconductor films by a solution coating process and the application of the thin organic semiconductor films to organic thin-film transistors.

PRIOR ART DOCUMENTS

Patent Documents

Patent Document 1: JP-A-2008-524846
Patent Document 2: JP-A-2008-524869

Non-Patent Documents

Non-patent Document 1: Reid J. Chesterfield, et al., J. Phys. Chem. B, 108(50), 19281 (2004)
Non-patent Document 2: Ichikawa et al., Appln. Phys. Lett., 89(11), 112108 (2006)

DISCLOSURE OF THE INVENTION

Problem to be Solved by the Invention

The above-mentioned organic semiconductor material, however, has low solubility in solvents, and in the formation of a thin organic semiconductor film by a solution coating process, the film occasionally became non-uniform in the coating step or drying step. It was, therefore, difficult to obtain a uniform large-area film, and to obtain a large-area film, it was necessary to form a thin organic semiconductor film by a vapor deposition process. As described above, under the current situation, no organic semiconductor material has been found to enable the formation of a film by a film printing process, and moreover, to facilitate the uniform formation of a thin organic semiconductor film over a large area by the film printing process.

Moreover, an organic thin-film transistor to be fabricated by using the above-mentioned perylene tetracarboxylic diimide or a derivative thereof as an organic semiconductor material requires the introduction of halogen atoms such as fluorine atoms in the structure of the derivative for providing it with high transistor performance. This leads to a need for the modification of the production process of the material into a more complex or multi-stage process, and therefore, involves a practical problem that the organic semiconductor material becomes costly and the fabrication of low price devices is rendered difficult from the standpoint of the material. There is, accordingly, an outstanding desire for the development of a technology, which facilitates the production of an organic semiconductor material without needing going through many steps, can produce it at lower cost and at the same time, with higher performance as an organic semiconductor material, can use a solution coating process, facilitates the uniform formation of a thin organic semiconductor film over a large area by a film printing process, and moreover, can use the thin film as an organic semiconductor layer or organic thin-film transistor having excellent electron mobility and ON/OFF ratio although it is a thin film formed by the simple process.

An object of the present invention is, therefore, to provide an extremely-useful, fine-particulate organic semiconductor material, which facilitates the uniform formation of a thin organic semiconductor film over a large area in accordance with a film printing process by not dissolving but dispersing a fine particulate material in a liquid medium to achieve a high concentration and using the dispersion, and also enables to form a thin organic semiconductor film with a high electron mobility and a high ON/OFF value.

Other objects of the present invention are to provide a thin organic semiconductor film and organic transistor, which use the above-described fine-particulate organic semiconductor material and are excellent in economy and performance. A still further object of the present invention is to provide an organic transistor comprised of a thin organic semiconductor film uniformized further through heat treatment.

Means for Solving the Problem

The above-described objects can be achieved by the present invention to be described hereinafter. Described specifically, the present invention provides a fine-particulate organic semiconductor material, which is in a form of fine particles and is usable as an organic semiconductor material, wherein the fine particles are fine thermotropic liquid crystal particles that undergo a phase transition into a liquid crystal state when heated to a temperature of from 50° C. to 350° C.

In the fine-particulate organic semiconductor material, the fine particles may preferably comprise a perylene tetracarboxylic diimide derivative represented by the following formula (1):

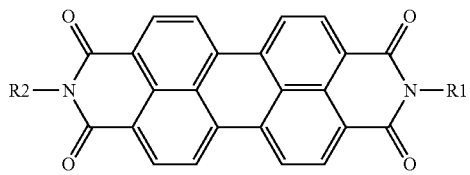

wherein R1 and R2 each independently mean a branched or unbranched alkyl group having from 1 to 22 carbon atoms, and may each independently contain one or more heteroatoms selected from N, O, S and P.

The derivative represented by the formula (1) may preferably be N,N'-ditridecyl perylene tetracarboxylic diimide represented by the following structural formula (1), or N,N'-bis(3-(n-dodecyloxy)-n-propyl)-3,4,9,10-perylene tetracarboxylic diimide represented by the following structural formula (2):

The phase transition into the liquid crystal state may preferably take place at a temperature of from 100° C. to 250° C. Further, the fine particles may preferably have an average particle size of from 10 nm to 10 μm.

The present invention also provides, in another aspect thereof, a thin organic semiconductor film formed from any one of the above-described fine-particulate organic semiconductor materials.

The present invention also provides, in a further aspect thereof, a dispersion for forming an organic semiconductor film, which is useful in forming the organic semiconductor film and comprises an organic solvent and any one of the above-described fine-particulate organic semiconductor materials dispersed in the organic solvent. As a preferred embodiment of the dispersion, the organic solvent may have a specific inductive capacity of from 2 to 60.

The present invention also provides, in a still further aspect thereof, a process for producing a thin organic semiconductor film, which comprises coating and drying the dispersion on a substrate, and then subjecting a resultant coating film to heat treatment at a temperature of from 50° C. to 350° C. such that the fine-particulate organic semiconductor material in the film are allowed to undergo a phase transition into a liquid crystal state to form a uniform thin organic semiconductor film on the substrate.

The present invention also provides, in an even still further aspect thereof, an organic thin-film transistor provided with a substrate and at least a gate electrode, gate insulating layer, thin organic semiconductor film, source electrode and drain electrode formed on the substrate, wherein the thin organic semiconductor film is the above-described thin organic semiconductor film or the thin organic semiconductor film formed by the above-described process.

Preferably, the thin organic semiconductor film to be applied to the above-described organic thin-film transistor may have been subjected to heat treatment at a temperature between from 70° C. and 250° C. In the above-described organic thin-film transistor, its electron mobility may be preferably from 0.0001 to 10 cm$^2$/Vs, more preferably from 0.0001 to 5.0 cm$^2$/Vs.

Advantageous Effects of the Invention

According to the present invention, there is provided a fine-particulate organic semiconductor material, which can form a thin organic semiconductor film with a high electron Structural formula (1)

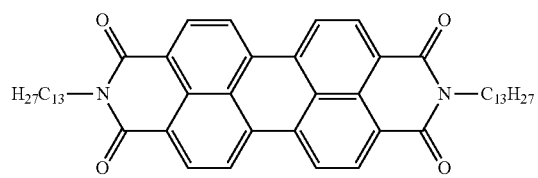

Structural formula (2)

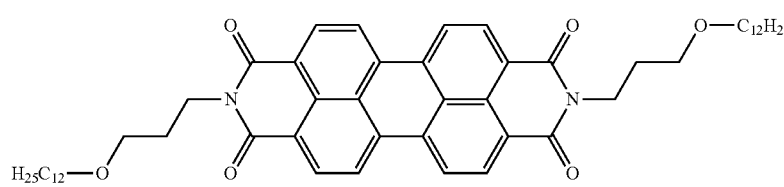

mobility and a high ON/OFF value. According to the present invention, the formation of the fine-particulate organic semiconductor material of the present invention into a dispersion in which the fine-particulate organic semiconductor material is dispersed in an organic solvent makes it possible to form a uniform thin organic semiconductor film over a wide area by a simple film-forming process that uses the dispersion. According to the present invention, the application of the above-described thin organic semiconductor film makes it possible to provide an organic thin-film transistor which is excellent in economy and transistor characteristics and is extremely useful.

MODES FOR CARRYING OUT THE INVENTION

Figure 1:
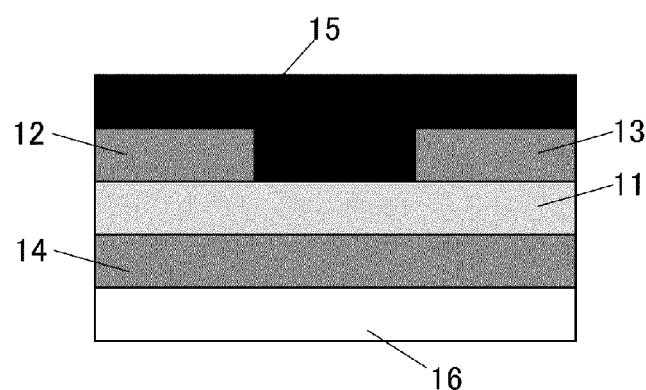
FIG. 1 is a cross-sectional view illustrating an example of the configuration of a bottom-contact organic thin-film transistor according to the present invention.

Preferred embodiments of the present invention will next be described in detail. It is, however, to be noted that the present invention is not limited to or by the following embodiments and can be practiced within a scope not departing from the gist of the present invention. A description will first be made about the fine-particulate organic semiconductor material of the present invention. It is to be noted that each "solvent" for use in the present invention shall have both an effect of usability as a dispersion medium for a solute and an effect of solubility for the solute in order to achieve the objects.

The fine particulate organic semiconductor material according to the present invention is a thermotropic liquid crystal which undergoes a phase transition into a liquid crystal state in a temperature range of from 50° C. to 350° C. Owing to the possession of thermotropic liquid crystallinity, the material of the present invention makes it possible to form a more uniform, thin organic semiconductor film of excellent performance through a heat treatment step.

As the fine-particulate material having the above-described characteristics, those to be described hereinafter can be specifically mentioned. Illustrative are phthalocyanines and their derivatives, such as metal-free phthalocyanines, copper phthalocyanines and cobalt phthalocyanines; perylenes and their derivatives, such as dimethyl perylene diimide, dioctyl perylene diimide, ditridecyl perylene diimide and dioctadecyl perylene diimide; naphthalene derivatives such as dioctyl naphthalene tetracarboxylic acid diimide; thiophenes and their derivatives, such as poly-3-hexylthiophene; acenes and their derivatives, such as pentacene, tetracene and anthracene; and graphene and porphyrin, and derivatives thereof.

The above-enumerated compounds have a π-conjugated skeleton structure and one or more alkyl groups and/or alkyl ether groups. As a result of a study, the present inventors found that upon heating, such a material undergoes a phase transition into a liquid crystal state and exhibits thermotropic crystallinity. If a material has thermotropic crystallinity, it can form a more uniform, thin organic semiconductor film of excellent performance through a heat treatment step, and is considered to be extremely useful industrially. Such a material can, therefore, be used without problem as a fine-particulate organic semiconductor material according to the present invention.

As particularly preferred, fine-particulate organic semiconductor materials in the present invention, perylene diimide derivatives can be mentioned. These perylene derivatives each contain, at each of the opposite ends thereof, two carbonyl groups in each of which an oxygen atom is bonded to a corresponding carbon atom via a double bond. As strong electron drawing property is produced by these carbonyl groups, the perylene derivatives act as n-type organic semiconductor materials. Therefore, the perylene derivatives are provided with a deep HOMO energy level, and have the possibility of providing organic thin-film transistors that exhibit stable transistor performance despite the existence of impurities, such as oxygen and water, contained in the atmosphere. Owing to strong intermolecular interaction of perylene skeleton structures themselves, which are each formed of aromatic rings, strong stacking is formed so that the perylene derivatives can exhibit characteristics as electron transport materials. Molecules of a perylene diimide derivative having alkyl groups orient perpendicularly to a substrate in the formation of an organic thin film on the substrate by a vapor deposition process or solution coating process, and achieve a high electron mobility because of the spreading of their perylene skeleton structures in a horizontal direction. Owing to the possession of the thermotropic liquid crystallinity, further uniformization of the film is feasible by subjecting the thin organic semiconductor film to heat treatment up to around its phase transition temperature so that its electron mobility also increases (for example, $\mu=2.1$ cm$^2$/Vs).

As the above-described perylene diimide derivatives, perylene tetracarboxylic diimide derivatives represented by the following formula (1) are particularly preferred.

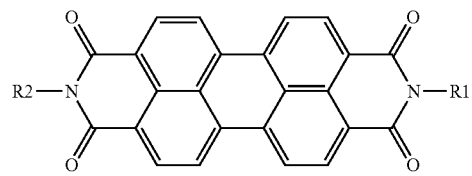

wherein R1 and R2 each independently mean a branched or unbranched alkyl group having from 1 to 22 carbon atoms, and may each independently contain one or more heteroatoms selected from N, O, S and P.

The dispersion of each organic semiconductor material represented by the formula (1) in an organic solvent makes it possible to stably form a thin organic semiconductor film by a dispersion coating process, as it has thermotropic liquid crystallinity and excellent dispersion stability owing to the inclusion of alkyl groups and/or alkyl groups, each of which contains one or more heteroatoms selected from N, O, S and P, at each of both end nitrogen atoms of the perylene tetracarboxylic diimide.

As the substituent groups (R1, R2) bonded to the respective end nitrogen atoms of each of the above-described perylene tetracarboxylic diimide derivatives represented by the formula (1), those to be described hereinafter are preferred. Illustrative are linear alkyl groups having from 1 to 22 carbon atoms, such as methyl, ethyl, butyl, propyl, heptyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl and docosyl, and their corresponding branched alkyl groups. As the substituent groups (R1, R2) of each of perylene tetracarboxylic diimide derivatives as other preferred fine-particulate organic semiconductor materials, branched or unbranched alkyl groups containing one or more hetero atoms, such as 3-methoxy-n-ethyl, 3-methoxy-n-propyl, 3-ethoxy-n-propyl, 4-ethoxy-n-butyl, 5-(n-butyloxy)-n-pentyl, 3-(n-butyloxy)-n-propyl, 3-(n-butyloxy)-n-hexyl, 3-(n-heptyloxy)-n-propyl, 3-(iso-butyloxy)-n-propyl, 3-(sec-butyloxy)-n-propyl, 3-(tert-butyloxy)-n-propyl, 3-(n-octyloxy)-n-propyl, 3-(n-decyloxy)-n-propyl, 3-(n-dodecyloxy)-n-propyl, 3-(n-tetradecaoxy)-n-propyl, 3-(n-eicosaoxy)-n-propyl, 2-(2-ethoxyethyloxy)ethyl, 2-(2-n-butyloxy)ethyl, 2-(2-n-hexyloxy)ethyl, 2-(2-n-octyloxy)ethyl, 2-(2-sec-octyloxy)ethyl, 2-(2-butoxypropyloxy)propyl, 2-(2-(dodecyloxy)propyloxy) propyl, 3-(n-butylthio)propyl, 3-(ethylthio)propyl, 3-(n-dodecylthio)propylamine, and 3-(n-dodecylselanyl)propyl, can be mentioned.

Taking into consideration the availability and reaction readiness of the raw materials, the semiconductor characteristics of the perylene tetracarboxylic diimide derivatives, and the like, preferably usable are those containing, as the substituent groups (R1, R2), any ones of octyl, nonyl, decyl, undecyl, dodecyl, tridecyl, tetradecyl, pentadecyl, hexadecyl, heptadecyl, octadecyl, 3-(n-butyloxy)-n-propyl, 3-(n-dodecyloxy)-n-propyl, and 3-(n-tetradecyloxy)-n-propyl.

The perylene tetracarboxylic diimide derivatives, which are suitable as the fine-particulate organic semiconductor material according to the present invention, can be synthesized by such a known process as will be described below. The perylene tetracarboxylic diimide derivatives useful in the present invention can each be obtained, for example, by reacting the corresponding perylene tetracarboxylic acid anhydride with the corresponding amine in an organic solvent of high boiling point or by once forming the corresponding perylene tetracarboxylic diimide into its potassium salt and then reacting it with the corresponding alkyl halide.

In the perylene skeletons of the perylene diimide derivatives preferred in the present invention, one or more of halogen atoms, such as fluorine, chlorine, bromine and iodine, and cyano groups can be introduced as needed.

Further, the fine-particulate organic semiconductor material according to the present invention can easily form an organic semiconductor film by coating. Relying upon the thin organic semiconductor film formed with the fine-particulate organic semiconductor material according to the present invention, it is possible to stably realize transistor characteristics in the atmosphere. By using a material of the formula (1) in which R1 and R2 are fluorine-substituted alkyl groups, the resulting thin film can prevent penetration of impurities such as water, oxygen and air, and therefore, can serve as a thin organic semiconductor film capable of stably exhibiting the n-type semiconductor characteristics.

As the perylene tetracarboxylic diimide derivatives represented by the formula (1), illustrative are N,N'-ditridecylperylene tetracarboxylic diimide represented by the following structural formula (1) and N,N'-bis(3-(n-dodecyloxy)-n-propyl)-3,4,9,10-perylene tetracarboxylic diimide represented by the following structural formula (2).

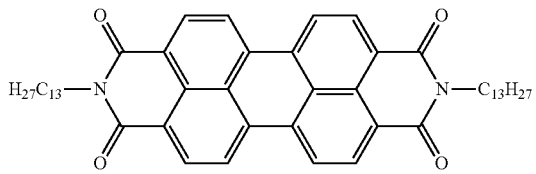

Structural formula (1)

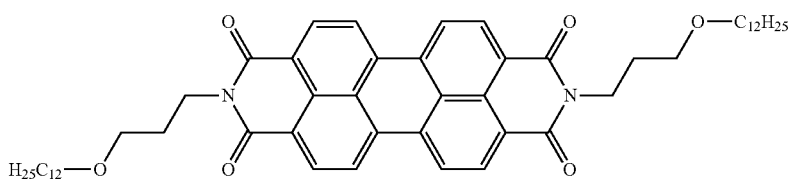

Structural formula (2)

As perylene tetracarboxylic acid anhydrides usable upon synthesis of the perylene tetracarboxylic diimide derivatives useful as the fine-particulate organic semiconductor material according to the present invention, the below-described perylene tetracarboxylic acid anhydrides can be mentioned. Examples include unsubstituted 3,4,9,10-perylene tetracarboxylic acid anhydride, 1,7-dicyano-3,4,9,10-perylene tetracarboxylic acid anhydride, 1,7-dichloro-3,4,9,10-perylene tetracarboxylic acid anhydride, 1,7-difluoro-3,4,9,10-perylene tetracarboxylic acid anhydride, 1,6,7,10-tetrafluoro-3,4,9,10-perylene tetracarboxylic acid anhydride, and the like. Taking into consideration the availability and reaction readiness of the raw materials, the semiconductor characteristics of the synthesized perylene tetracarboxylic diimide derivatives, and the like, it is preferred to use, among those described above, the unsubstituted perylene tetracarboxylic acid anhydride with no substituent group or groups introduced on its perylene skeleton.

For using the thin organic semiconductor film, which has been formed using the fine-particulate organic semiconductor material according to the present invention, in the organic thin-film transistor, it is preferred to use the compound in a purified form. Described specifically, a reduction of impurities will decrease causes that inhibit the movement of electrons through the resulting thin organic semiconductor film, and will provide the resulting organic thin-film transistor with an increased electron mobility, and therefore, with improved transistor performance. No particular limitation is imposed on a method for increasing the purity, but it is effective to use the compound after increasing its purity by using a purification method such as chromatography, recrystallization, sublimation purification, zone refining or supercritical purification, or by using two or more of these methods in combination.

The organic thin-film transistor according to the present invention can be formed by using the fine-particulate organic semiconductor material according to the present invention in the thin organic semiconductor film. As the fine-particulate organic semiconductor material according to the present invention, a single fine-particulate organic semiconductor material may be used, or plural materials of different kinds may be used in combination. Further, perylene and its derivatives and naphthalene diimide and its derivatives may also be used in combination. Upon forming the thin organic semiconductor film according to the present invention, however, it is desired to set the content of the fine-particulate organic semiconductor material according to the present invention in the total amount of organic materials preferably at 20 mass % or higher, more preferably 50 mass % or higher, still more preferably 90 mass % or higher. A content lower than 50 mass % leads to difficulty in forming a uniform film, and hence, in obtaining a film thickness sufficient as a thin organic semiconductor film, and a content lower than 20 mass % leads to difficulty in obtaining a stable thin organic semiconductor film.

As a method for forming the fine-particulate organic semiconductor material according to the present invention, any method can be used without problem insofar as it can obtain fine particles. It is possible to use a fine particle production method for pigments, such as, for example, the acid paste method that dissolves such a semiconductor material as described above in sulfuric acid, and then allows it to deposit in water, the solvent milling method that controls the crystal growth of a pigment in an organic solvent, the dry milling method, the dry salt milling method, or a method that grinds such a semiconductor material as described above together with salt into fine particles in a kneader. For the control of the particle size, the solvent method, emulsion treatment or the like can be also used in combination. As a preferred method for the formation of the fine-particulate organic semiconductor material, it is possible to use the liquid phase method that dissolves the organic semiconductor material in a basic solution or acidic solution, and with an acidic solution or alkaline solution which does not dissolve the organic semiconductor material, then allows the organic semiconductor material to deposit such that fine particles are obtained.

The fine-particulate organic semiconductor material obtained by the liquid phase method can be converted to an amorphous form having no distinct crystal system. A thin organic semiconductor film formed with the amorphous fine-particulate organic semiconductor material can be formed into a thin organic semiconductor film, which is more uniform that one formed from particles having a crystal system, by subjecting it to heat treatment. As another preferred method for the formation of fine organic semiconductor particles, the laser aberration method can be mentioned. This method performs aberration treatment with a laser, and can adjust the particle size by controlling conditions (for example, the concentration of a dispersion, the kind of a dispersion solvent, laser output, treatment time). Therefore, it is possible to obtain fine particles the particle sizes of which are small and uniform, and hence, to form a uniform thin organic semiconductor film by solution coating.

The dispersion according to the present invention, which is suited for the formation of the thin organic semiconductor film according to the present invention, can be obtained by dispersing the above-mentioned fine-particulate organic semiconductor material in an organic solvent. Any organic solvent can be used, without any particular limitation, as an organic solvent for use upon conducting the above-mentioned dispersion, insofar as a dispersion of adequate concentration can be obtained. Examples include halogenated hydrocarbon solvents such as chloroform, dichloroethane, chlorobenzene, dichlorobenzene, trichlorobenzene and chloronaphthalene; ketone solvents such as acetone, methyl ethyl ketone and methyl isobutyl ketone; ester solvents such as ethyl acetate and butyl acetate; alcohol solvents such as methanol, ethanol, n-propanol, isopropanol, n-butanol, sec-butanol, isobutanol, tert-butanol and n-hexanol; ether solvents such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether ethylene glycol, diethylene glycol, triethylene glycol diethyl ether, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, triethylene glycol diethyl ether, triethylene glycol dibutyl ether, propylene glycol monomethyl ether and propylene glycol dimethyl ether; aromatic hydrocarbon solvents such as toluene, xylene and ethylbenzene; and aprotic polar solvents such as tetrahydrofuran, sulfolane, N,N-dimethylformamide, N-methyl-2-pyrrolidone, dimethyl sulfoxide and acetonitrile. These solvents may be used either singly or in a combination of plural ones. Water may also be used in combination insofar as it is used together with the above-described organic solvent or solvents.

Especially when dispersion stability is required for the fine particle dispersion, it is preferred to use an organic solvent having a specific inductive capacity of from 2 to 60 and capable of stably retaining charges of the fine particles, especially preferably an organic solving having a specific inductive capacity of from 30 to 60. The use of a solvent having a specific inductive capacity of from 30 to 60 (for example, acetonitrile: 37.5) makes it possible to obtain a dispersion, which remains stable over a long term, irrespective of the particle size of the fine organic semiconductor particles. When a solvent having a specific inductive capacity of from 10 to 30 (for example, dichloroethane: 10.5, ethanol: 24.3) is used, the stability may be lowered to result in separation of the dispersion. Even such a dispersion can be used without problem insofar as it can be coated on a substrate. Further, the use of a concentrated portion of the separated dispersion provides a dispersion of high concentration, which enables to form an organic semiconductor film of large thickness. A specific inductive capacity of smaller than 2 involves a problem in that the dispersion stability is lowered to form large aggregates and no uniform thin organic semiconductor film can be formed. A specific inductive capacity of greater than 60, on the other hand, means high hydrophilicity, thereby raising a problem such as absorption of moisture in the solvent. It is to be noted that the above-described specific inductive capacities are all literature values.

In the preparation of such fine particles, a low-molecular surfactant or high-molecular surfactant, a dispersant, or an inorganic compound such as silica can also be used as needed to avoid aggregation of fine particles in the dispersion.

Concerning the organic solvent for dispersing the fine-particulate organic semiconductor material according to the present invention, no particular limitation is imposed on the solubility of the material in the solvent, and any organic solvent can be used without problem insofar as the formation of a thin organic semiconductor film is feasible. However, the provision of the fine-particulate organic semiconductor material with a high solubility involves a potential problem that the resulting thin organic semiconductor film may not exhibit charge transport characteristics. Therefore, the solubility may preferably be 5 mass % or lower, with 1 mass % or lower being preferred in the case of a thin organic semiconductor film required to exhibit still greater charge transport characteristics.

As a result of dissolution of the fine-particulate organic semiconductor material in a solvent, crystal growth may occur to form coarse particles, thereby possibly making it difficult to form a thin organic semiconductor film. In such a case, it is preferred to use an organic solvent in which the solubility of the fine-particulate organic semiconductor material is 0.1 mass % or lower, with 0.01 mass % or lower being more preferred. There is no particular lower limit on the solubility of the organic pigment in such a poor solvent.

As a method for the production of the fine particle dispersion according to the present invention, it can be prepared by an ordinary dispersion method for fine particles. In the dispersion method for fine particles, a bead mill, ball mill, roll mill, bucket-type mill, ultrasonic dispersion machine, high-pressure dispersion machine or the like can be used without any particular limitation. As a particularly preferred production method, there is a method that mixes coarse particles in an organic solvent to be used and then produces fine particles by the laser aberration method in the organic solvent.

The fine-particulate organic semiconductor material according to the present invention can be used for the formation of the thin organic semiconductor film according to the present invention irrespective of its particle size, but may preferably have a particle size of from 10 nm to 10 μm. A particle size of smaller than 10 nm is not preferred, because an organic semiconductor film to be formed through a coating step or printing step is provided with a small thickness, leading to a potential problem that a uniform film may not be obtained stably. On the other hand, a particle size of greater than 10 μm is not preferred either, because the resulting dispersion of the fine-particulate semiconductor material has low stability, leading to a potential problem that the semiconductor material may settle, and moreover, the formation of a film by coating or printing may be rendered difficult and the film, even if formed, may not function stably.

The concentration of the dispersion in which the fine-particulate organic semiconductor material is dispersed in the liquid solvent may be preferably 0.001 mass % or higher, more preferably 0.01 mass % or higher. There is no particular upper limit on the concentration of the organic semiconductor material in the solvent, and the dispersion can be used without problem insofar as it has a concentration sufficient to provide a viscosity suited for a coating machine or printing machine that forms the thin organic film.

The thin organic semiconductor film according to the present invention, which is formed from the fine-particulate organic semiconductor material according to the present invention, can be provided as a still better film of excellent performance by coating the fine-particulate organic semiconductor material on a substrate and then conducting heating. For example, a more uniform, thin organic semiconductor film of excellent performance can be formed by printing or coating a dispersion, in which the fine-particulate organic semiconductor material is dispersed in a liquid solvent, on a substrate and then conducting heating. This coating method of fine particles enables to further simplify the apparatus and to further reduce the cost, to form a thin organic semiconductor film over a large area, and to obtain a uniform and sufficient film thickness. As a printing method to be used in the foregoing, a known printing method can be used. Examples include spin coating, printing methods such as inkjet printing, screen printing, planographic printing, letterpress printing and intaglio printing, an air spray method that by the principle of atomization, coating is performed with compressed air, a static electricity applied spray method, an airless spray method, and the like. By such a method, the thin organic semiconductor film (coating film) of the fine-particulate organic semiconductor material can be formed on the substrate. As an alternative method for the formation of the thin organic semiconductor film according to the present invention, the thin organic semiconductor film (coating film) of the fine-particulate organic semiconductor material can be formed by an electrostatic powder coating method or the like that electrically charges the fine-particulate organic semiconductor material which has 100% solid content without using any solvent such as an organic solvent or water, and then applies the charged fine-particulate organic semiconductor material onto an electrically-grounded substrate (which may be heated) under static electricity. This method is one of preferred methods from the standpoints of environment and cost because it does not include a solvent removal step and requires fewer steps.

Figure 7:
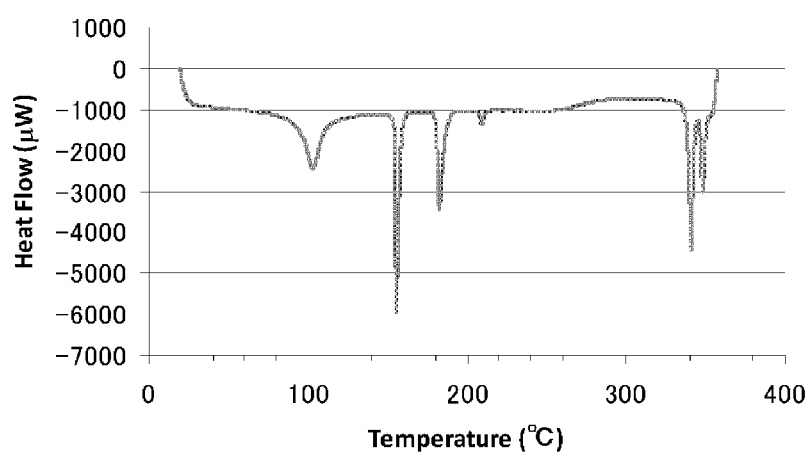
FIG. 7 is a variation diagram of a heat flow of N,N'-tridecyl-3,4,9,10-perylene tetracarboxylic diimide as measured by differential scanning calorimetry.

Variations in the heat flow of N,N'-tridecyl-3,4,9,10-perylene tetracarboxylic diimide, which can be used as the fine-particulate organic semiconductor material according to the present invention, as measured by differential scanning calorimetry (hereinafter abbreviated as "DSC") are shown in FIG. 7. As indicated in FIG. 7, it can be confirmed that because of the inclusion of tridecyl groups as long-chain alkyl groups, endotherms occurred around 102° C., 155° C., 182° C. and 209° C., respectively, and a phase transition took place.

Further, the phase change of the fine-particulate organic semiconductor material by a temperature change, said phase change being essential for the formation of a still better thin organic semiconductor film according to the present invention, can be obtained by providing it with the below-described structure. Described specifically, owing to the inclusion of one or more hetero atoms in each of the two alkyl chains bonded to perylene tetracarboxylic diimide, the fine-particulate organic semiconductor material is considered to undergo a phase transition into a liquid crystal phase (smectic liquid crystal) in the temperature range of from 50° C. to 350° C. About the phase changes of long-chain alkyl perylene tetracarboxylic diimides, a description is found in C. W. Struijk et al., J. Am. Chem. Soc. 122 (2000).

The present inventors previously reported that the heat treatment of a thin organic semiconductor film, which is formed of a perylene tetracarboxylic diimide derivative, around its phase change temperature provides the resulting organic thin-film transistor with improved transistor performance (Non-patent Document 2 cited above).

It has been considered that a thin organic semiconductor film (coating film) formed by coating a dispersion of fine organic semiconductor particles according to the present invention has a polycrystalline structure formed of fine crystals aggregated together and without any further treatment or the like, includes many crystal grain boundaries and defects and that the existence of these crystal grain boundaries and defects inhibits the transport of charges. In the present invention, however, the thin film (coating film) formed with the fine-particulate organic semiconductor material is brought into a liquid crystal state through heat treatment, and subsequently, is cooled to take a crystalline state. Therefore, upon taking the crystalline state again, the transistor characteristics are improved, in other words, the electron mobility is increased by a combined action of [1] the formation of a strongly stacked state through a rearrangement of molecules, [2] the elimination of impurities upon crystallization, [3] an increase in grain size and a reduction in crystal grain boundaries, defects and deficiencies, [4] enhanced close contact with electrodes, and so on.

As the fine-particulate organic semiconductor material according to the present invention has thermotropic crystallinity, further uniformization of a film can be achieved through a heat treatment step in a temperature range, in which the fine-particulate organic semiconductor material is brought into a smectic liquid crystal or nematic liquid crystal, after the fine-particulate organic semiconductor material according to the present invention is printed or coated on a substrate. The fine-particulate organic semiconductor material according to the present invention is characterized in that it is a thermotropic liquid crystal which undergoes a phase transition into a liquid crystal state of either a smectic liquid crystal or a nematic liquid crystal in the temperature range of from 50° C. to 350° C. A phase transition temperature of lower than 50° C. involves a possibility that the transistor characteristics may substantially vary depending on the temperature environment in which the resulting thin organic semiconductor film is used as an organic thin-film transistor. A phase transition temperature of higher than 350° C., on the other hand, makes it difficult to use a plastic-made substrate, and moreover, makes it difficult to perform the fabrication by low-cost and economical facilities the usability of which is one of merits of the organic semiconductor material.

As a particularly preferred material, it preferably undergoes a phase transition into a liquid crystal state in a temperature range of from 70° C. to 250° C. As a temperature range in which especially preferred thermotropic liquid crystallinity is exhibited, a range of from 70° C. to 200° C. can be mentioned because an organic transistor may be formed on a flexible plastic-made substrate in addition to the standpoint of cost and the standpoint of transistor performance.

As the atmosphere of an environment in which the heat treatment is conducted, the heat treatment can be conducted in or under any one of an air atmosphere, an inert gas such as nitrogen or argon, and vacuum. It is more preferred to conduct the heat treatment in a vacuum atmosphere or an inert gas atmosphere, because the individual materials can be protected from deterioration, oxidation or the like.

No particular limitation is imposed on a heat treatment method, and an oven, hot roll, hot press or the like can be used. As an alternative, the heat treatment and drying can be conducted together in a drying zone after the thin organic semiconductor film is formed by printing. Although no particular limitation is imposed on the time of the heat treatment insofar as the thin organic semiconductor film is allowed to reach a predetermined temperature, the time of the heat treatment may desirably be 24 hours or shorter as long-time heat treatment accelerates a deterioration of the substrate.

By holding the thin organic semiconductor film, which is comprised of the fine-particulate organic semiconductor material according to the present invention, in the vapor of an organic solvent, realignment of the fine organic semiconductor particles occurs to afford a more uniform and smooth film. As such a solvent, the solvents enumerated above for use in dispersion can be used without problem. As particularly preferred solvents, however, halogen-containing organic solvents such as chloroform, trichloromethane and trichloroethylene, pyridine, n-methylpyrrolidone, toluene, xylene and the like can be mentioned. As a method for the treatment with the solvent, there is a method that holds the thin organic film in a closed vessel with the solvent contained therein, a method that the vapor of the solvent is blown against the thin organic film, or the like.

The above-mentioned compound represented by the formula (1) exhibits characteristics as an n-type organic semiconductor material, and the use of the compound as a thin organic semiconductor film makes it possible to fabricate a more useful, organic thin-film transistor. A more detailed description will hereinafter be made about the organic thin-film transistor according to the present invention. It should, however, be borne in mind that the present invention is not limited to these structures.

As the structure of an organic thin-film transistor, the MIS structure (Metal-Insulator-Semiconductor structure) that a gate electrode is insulated by an insulating film is often used in general. An organic thin-film transistor to which the present invention can be applied has an organic semiconductor layer formed of a thin organic semiconductor film, and is further comprised of a source electrode, a drain electrode, a gate electrode and a gate insulating layer. In the organic thin-film transistor according to the present invention, the thin organic semiconductor film is formed with the fine-particulate organic semiconductor material.

Figure 2:
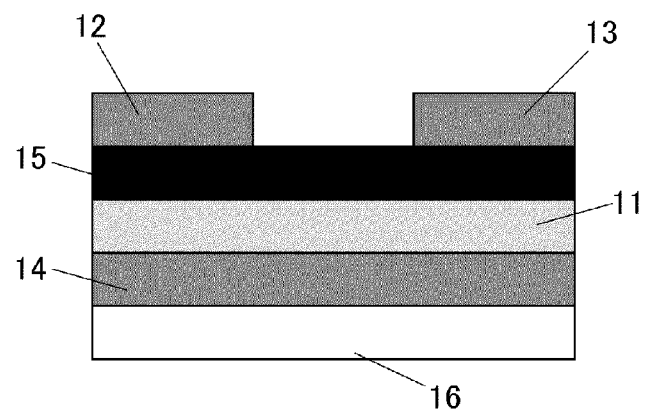
FIG. 2 is a cross-sectional view illustrating an example of the configuration of a top-contact organic thin-film transistor according to the present invention.

A description will next be made about the configuration of the organic thin-film transistor according to the present invention. FIGS. 1 and 2 are cross-sectional views illustrating different examples of the structure of the organic thin-film transistor according to the present invention, respectively. In the configuration of the organic thin-film transistor of FIG. 1, a gate electrode 14 is arranged on a substrate 16, an insulating layer 11 is stacked on the gate electrode, a source electrode 12 and a drain electrode 13 are formed with a predetermined interval therebetween on the insulating layer 11, and further, a thin organic semiconductor film 15 is stacked on the insulating layer 11, source electrode 12 and drain electrode 13 to form a bottom-gate, bottom-contact configuration. In the configuration of the organic thin-film transistor of FIG. 2, a gate electrode 14 is arranged on a substrate 16, an insulating layer 11 is stacked on the gate electrode, a thin organic semiconductor film 15 is stacked on the insulating layer 11, and further, a source electrode 12 and a drain electrode 13 are formed with a predetermined interval therebetween on the thin organic semiconductor layer 15 to form a bottom-gate, top-contact configuration.

The transistor device having one of such configurations performs a switching operation when a voltage is applied between the gate electrode and the source electrode and by the voltage so applied, the thin organic semiconductor film forms a channel region to control an electric current that flows between the source electrode and the drain electrode.

A description will next be made about the substrate that forms the organic thin-film transistor of the present invention. As the material that forms the substrate, any material can be used insofar as it is a material having insulating properties. Usable examples include substrates made of inorganic materials such as glass and alumina, and plastic-made substrates such as polyimide film, polyester film, polyethylene film, polystyrene film, polypropylene film and polycarbonate film. The use of a plastic-made substrate makes it possible to fabricate a lightweight, flexible organic thin-film transistor of excellent impact resistance. These substrates may be used either singly or in combination. It is to be noted that, when an electrically-conductive substrate, for example, silicon is used as a substrate material, the substrate can also serve as a gate electrode.

A description will next be made about the gate insulating layer that forms the organic thin-film transistor according to the present invention. Examples of a material that forms the gate insulating layer in the present invention include, but are not specifically limited to, inorganic materials such as $SiO_2$, $ZrO_2$, $Ta_2O_5$, $La_2O_3$, $Al_2O_3$ and $HfO_2$. As high-molecular insulating film materials, on the other hand, organic materials such as polyimides, polymethyl methacrylate, polyvinyl alcohol, polyvinyl chloride, polyacrylonitrile, polyvinylidene fluoride, polyethylene terephthalate, polyethersulfone and polycarbonates can be used. These insulating materials useful as gate insulating layers may be used either singly or in combination.

No particular limitation is imposed on a process for forming such a gate insulating layer. Illustrative are dry processes such as vapor deposition, CVD, sputtering and atmospheric-pressure plasma processing; and wet processes such as coating processes such as spray coating, spin coating, blade coating, dip coating, casting, roll coating, bar coating, die coating, air knife coating, slide hopper coating and extrusion, various printing processes, and inkjet printing. Depending on the properties of materials to be used, a desired process can be selected and applied as desired. For example, $SiO_2$ may be formed as a layer on a silicon substrate by thermal oxidation, steam oxidation or plasma oxidation.

A gate insulating layer may be hydrophobized by chemical surface treatment to improve the compatibility between the gate insulating layer and a thin organic semiconductor film, so that a uniform, thin organic semiconductor film can be formed to reduce a leak current. Although not particularly limited, such a hydrophobizing layer can be formed by solution coating or vacuum film-forming of a silane coupling agent such as, for example, OTS (octadecyltrichlorosilane), ODS (octadecyltrimethoxysilane) or HMDS (hexamethyldisilazane) or a fluorine-containing alkyl silane coupling agent on the gate insulating layer.

A description will next be made about electrode materials for forming the organic thin-film transistor according to the present invention. As electrode materials for use in the source electrode, drain electrode and gate electrode, materials having electrical conductivity are used. Usable examples include metal materials such as gold, silver, copper, platinum, aluminum, lithium, sodium, potassium, magnesium, calcium, titanium, indium, palladium, manganese, molybdenum, magnesium, calcium, barium, chromium, tungsten, tantalum, nickel, cobalt, copper, iron, lead and tin, and alloys of these metal materials; electrically-conductive oxides such as $InO_2$, $ZnO_2$, $SnO_2$, indium tin oxide (hereinafter abbreviated as "ITO") and indium zinc oxide (hereinafter abbreviated as "IZO"); carbon materials such as carbon black, fullerene, carbon nanotubes and graphite; and electrically-conductive high-molecular compounds. More preferred are gold, aluminum, magnesium, calcium, ITO, IZO and gold/chromium alloy as they each have small electric resistance at the surface of contact with the thin organic semiconductor film.

No particular limitation is imposed on a process for the formation of these electrodes. For example, they can be formed by using a process such as a printing process making use of a dispersion of an electrically-conductive material in a solution, a printing process making use of a solution of an electrically-conductive material in a solution, a vapor deposition process, or a sputtering process.

The source electrode and the drain electrode are arranged opposite each other. The inter-electrode distance (channel length) is one of parameters that determine transistor characteristics. An inter-electrode distance (channel length) not greater than 5,000 μm is generally usable without problem, with 1,000 μm or smaller being preferred. As the width between the source electrode and the drain electrode (channel width), any width can be used without any particular limitation, but 1 mm or smaller is preferred. However, a still longer channel width may be formed when the electrodes are formed in a comb-shaped structure. The source electrode and drain electrode so formed can be used without problem insofar as they have a thickness in a range of from several nanometers to several hundreds micrometers. More preferably, however, the thicknesses of the source electrode and drain electrode may range from 30 nm to 200 μm.

The organic thin-film transistor according to the present invention may be provided on the entire part or a part of its outer circumferential surface with a gas barrier layer to reduce the effects of oxygen, water and the like in the atmosphere. Examples of a material that forms such a gas barrier layer include polyvinyl alcohol, ethylene-vinyl alcohol copolymer, polyvinyl chloride, polyvinylidene chloride, polytetrafluoroethylene and the like.

The organic thin-film transistor according to the present invention can be evaluated for transistor characteristics by electron mobility ($cm^2/Vs$), ON/OFF ratio and threshold voltage (V). To obtain a large current through the organic thin-film transistor, it is particularly important that its electron mobility has a large value. The electron mobility may desirably be 0.0001 $cm^2/Vs$ or higher. When organic thin-film transistors have an electron mobility of 0.001 $cm^2/Vs$, they can be used as memory cells or drive elements for electron paper displays. When organic thin-film transistors have an electron mobility of 0.01 $cm^2/Vs$ or higher, they can be used as drive elements for active matrices as replacements for amorphous silicon transistors.

EXAMPLES

Examples of the present invention will hereinafter be described.

Production Example 1

Synthesis of Compound A

Firstly, perylene tetracarboxylic acid anhydride (3.9 g), tridecylamine (4.4 g) and anhydrous zinc acetate (0.6 g) were dispersed in N-methyl-2-pyrrolidone (50 mL), followed by stirring at 160° C. for 4 hours under a nitrogen gas stream. The reaction mixture was allowed to cool, and was then filtered. The resulting filter cake was washed with a mixture of methanol and dilute hydrochloric acid and with water in this order. Subsequently, the filter cake was dried to afford N,N'-tridecyl-3,4,9,10-perylene tetracarboxylic diimide (5.90 g, yield: 70%). The thus-afforded compound was isolated by column chromatography, and was purified by recrystallization to obtain PTCDI-C13 (Compound A) as coarse particles. Endothermic peaks by differential scanning calorimetric thermal analysis (DSC) (measured from room temperature to 250° C.): 102° C., 155° C., 182° C. and 209° C. (see FIG. 7).

Example 1

Preparation of Dispersion A1

Figure 3:
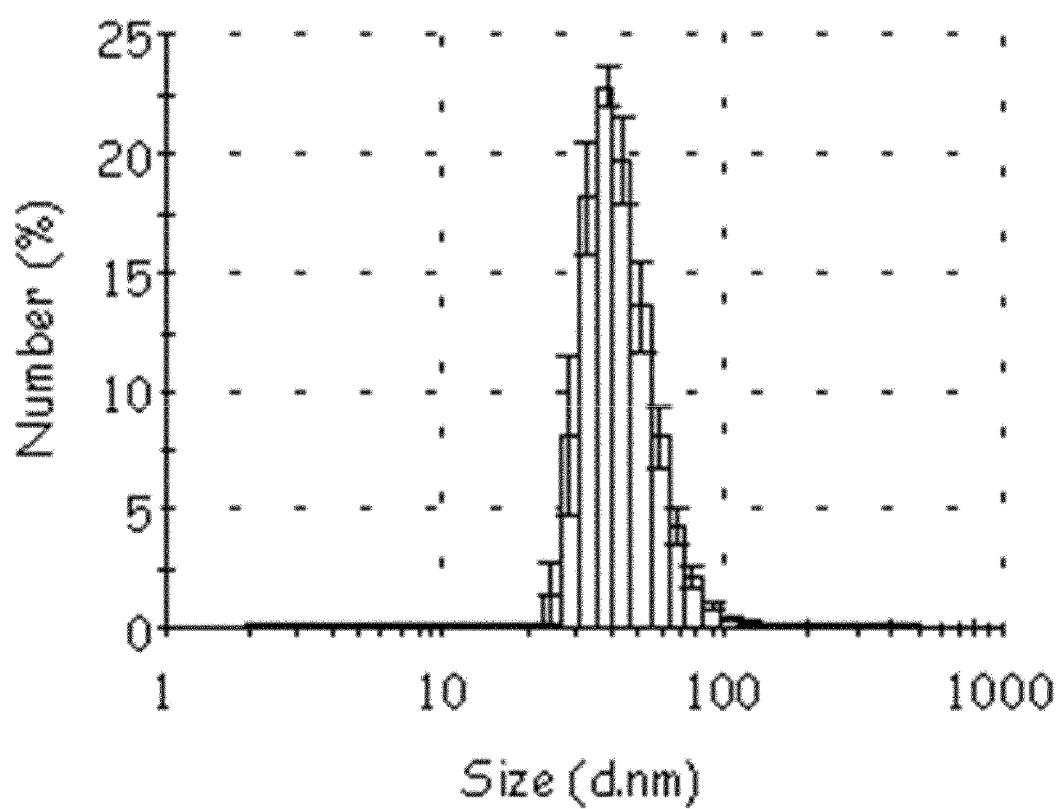
FIG. 3 is a particle size distribution diagram of a dispersion of a fine-particulate organic semiconductor material, which was used in Example 1, as measured by a laser diffraction particle size distribution analyzer.
Figure 4:
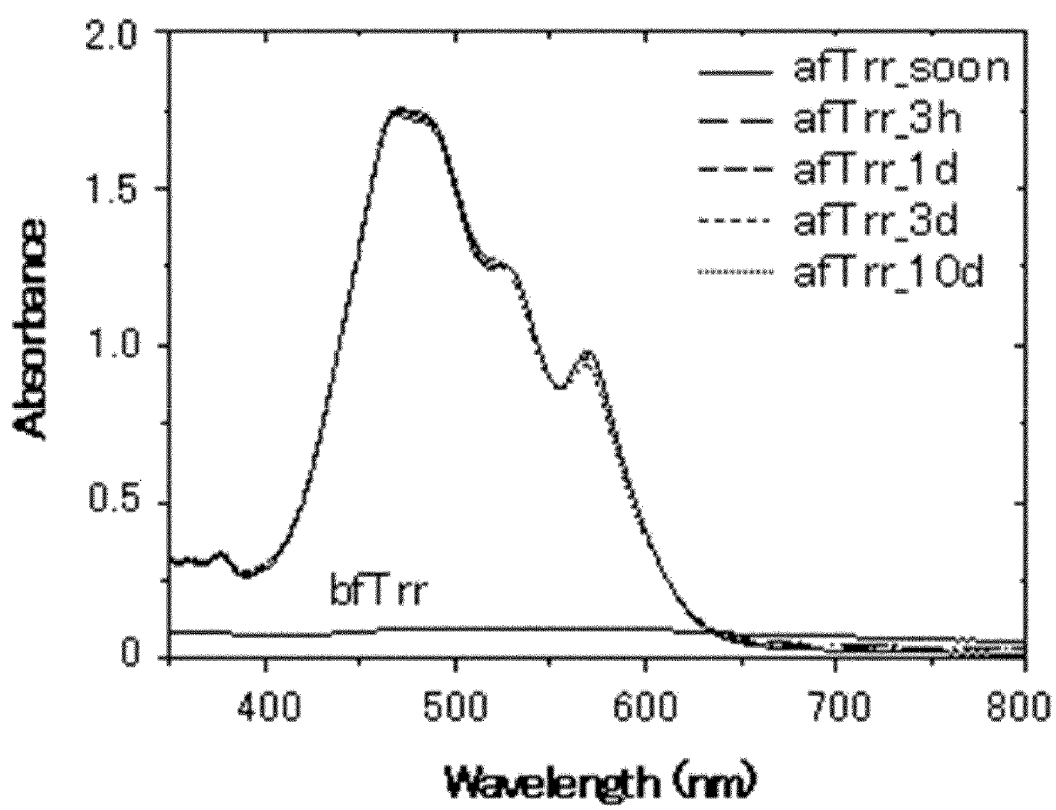
FIG. 4 is a diagram showing time-dependent variations in the visible light absorption characteristics of the dispersion of the fine-particulate organic semiconductor material, which was used in Example 1.

Compound A obtained as described above was mixed to acetonitrile (specific inductive capacity: 37.5) to give 0.01 mass %, and by the laser aberration method (wavelength: 532 nm, intensity: 100 mJ/cm$^2$, exposure time: 10 minutes), a fine particle dispersion was prepared. Dispersion A1 so obtained had an average particle size of 45 nm and a standard deviation of 14 nm (the dynamic light scattering method). The particle size distribution of the dispersion is shown in FIG. 3. Further, the absorption characteristics of the dispersion were measured by a UV-visible spectrophotometer. Changes in the absorption characteristics before the dispersion (bfTrr), soon after the dispersion (afTrr_soon), 3 hours after (afTrr 3 h), 1 day after (afTrr 1 d), 3 days after (afTrr 3 d) and 10 days after (afTrr 10 d) are shown, respectively, in FIG. 4.

Example 2

Preparation of Dispersion A2

Compound A obtained as described above was mixed to ethanol (specific inductive capacity: 24.3) to give 0.05 mass %, and by the laser aberration method (wavelength: 532 nm, intensity: 150 mJ/cm$^2$, exposure time: 10 minutes), a fine particle dispersion was prepared. After the resultant dispersion was allowed to stand for 10 days, the supernatant was discarded and the liquid mixture separated as a lower layer was provided as Dispersion A2.

Example 3

Preparation of Dispersion A3

Compound A obtained as described above was mixed to dichloroethane (specific inductive capacity: 10.5) to give 0.05 mass %, and by the laser aberration method (wavelength: 532 nm, intensity: 130 mJ/cm$^2$, exposure time: 10 minutes), a fine particle dispersion was prepared. Dispersion A3 so obtained had an average particle size of 250 nm and a standard deviation of 140 nm (the dynamic light scattering method).

Example 4

Preparation of Dispersion A4

Compound A obtained as described above was mixed to acetonitrile (specific inductive capacity: 37.5) to give 0.1 mass %, and by the laser aberration method (wavelength: 532 nm, intensity: 100 mJ/cm$^2$, exposure time: 10 minutes), a fine particle dispersion was prepared. Dispersion A4 was excellent in dispersion stability, and its UV-visible absorption characteristics remained unchanged from soon after the preparation until 30 days after the preparation.

Dispersions A1 to A4 prepared as described above were coated on substrates, respectively, and in a vacuum oven controlled at 40° C., were dried for 1 hour to fabricate devices. As electrodes for the devices, ITO or gold was used, and the channel width was set at 20 μm and 10 μm. The devices were measured for transistor characteristics under high vacuum, and subsequent to heat treatment, their transistor characteristics were measured again. The heat treatment was conducted at a set temperature of from 100 to 160° for 10 hours in a vacuum oven.

Evaluation of Thin-Film Transistors

Electrical characteristics of each thin film transistor were measured at room temperature under vacuum by "AGILENT B1500A". Concerning $I_D$ (drain current)-$V_D$ (drain voltage) characteristics, $V_D$ was swept in a direction of from 0 to 100 V and $V_G$ (gate voltage) was applied at intervals of 20 V from 100 to 0V. $I_D$-$V_G$ characteristics were measured by sweeping $V_G$ from 0 to 100 V at $V_D$=100 V.

From the linear region of $(I_D)^{1/2}$-$V_G$ characteristics and the equation (1), the mobility (μ) was calculated.

$$I_D = \frac{W}{2L} C_i \mu (V_G - V_T)^2 \qquad \text{Equation (1)}$$

In the above equation (1), $C_i$ is the capacitance (nF/cm$^2$) of a gate dielectric, and $V_T$ is a threshold voltage. Based on the slope of the $(I_D)^{1/2}$-$V_G$ characteristics, the field effect mobility was determined by using the equation (1), and from the intercept of the fitting line with the X-axis, the voltage was calculated.

Example 5

Fabrication of Organic Transistor with Dispersion A1

A silicon substrate, which had on a surface thereof a silicon oxide film (thickness: 200 nm) to be used as a gate insulating layer, was provided. An ITO film (150 nm) was formed by sputtering, and a source electrode and drain electrode were patterned using photolithography and wet etching. At that time, the channel length and channel width were 10 μm and 1,000 μm, respectively. Subsequently, a PDMS (polydimethylsiloxane) sheet with a hole formed therethrough was brought into close contact with the substrate. Dispersion A1 of Example 1 was filtered through a syringe filter (0.45 μm), and was then cast as much as 10 μL in the hole to form a thin organic semiconductor film on the silicon substrate. Drying and heat treatment was performed at 50° C. for 1 hour in vacuum.

Figure 5:
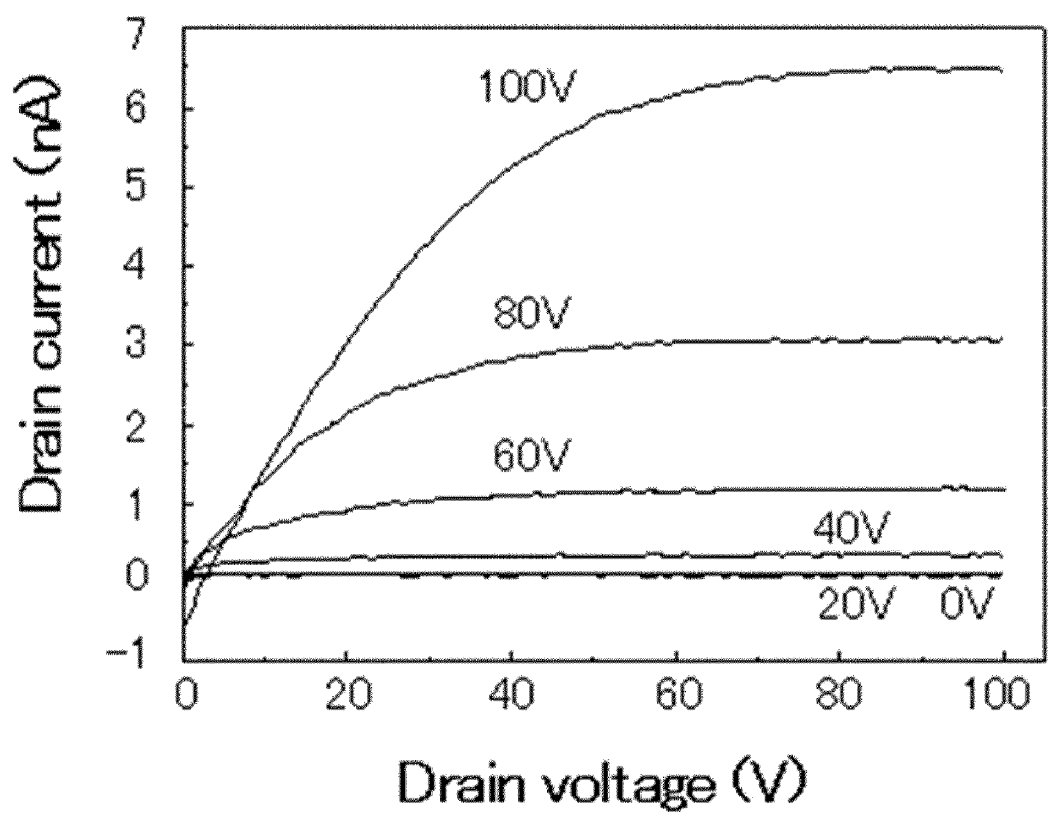
FIG. 5 is a diagram showing a relationship between current modulation characteristics (drain current and drain voltage) of Example 5.
Figure 6:
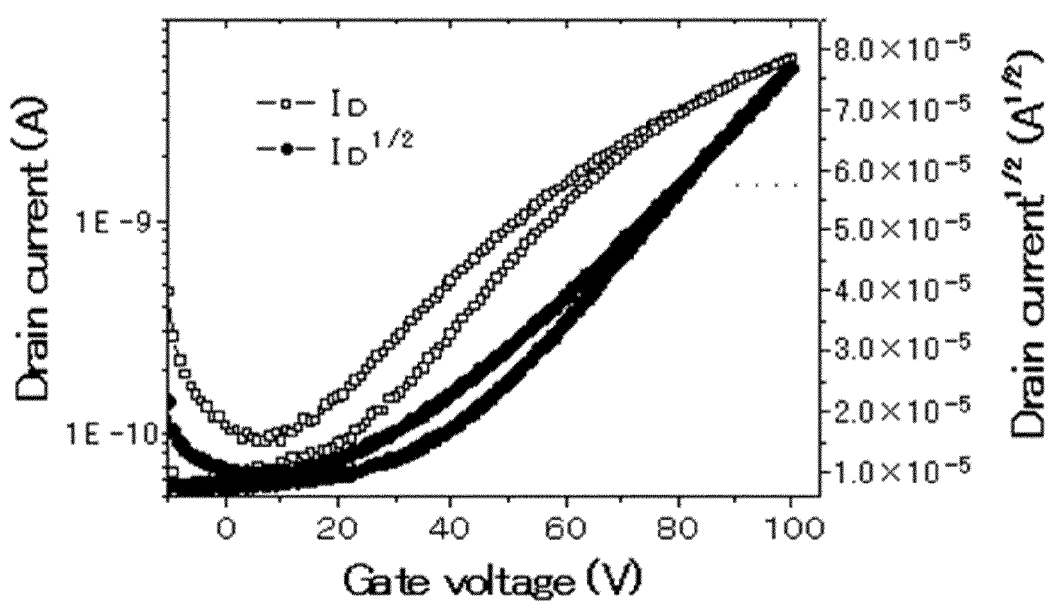
FIG. 6 is a diagram showing a relationship between current modulation characteristics (drain current and gate voltage) of Example 5.

With respect to the transistor obtained as described above, the drain voltage and drain current were measured at different gate voltages, respectively. As pronounced saturation regions were observed on the drain current-drain voltage curves as shown in FIG. 5, it was indicated that the transistor would be drivable as a field-effect transistor having typical n-type characteristics. The electron mobility, threshold voltage value and ON/OFF ratio calculated as transistor characteristic values from the drain current-drain voltage curves were 10.7×10$^{-6}$ cm$^2$/Vs, 32 V and 10$^2$, respectively. The results are shown in Table 1.

Example 6

Fabrication of Organic Transistor with Dispersion A2

Similar to Example 5, an organic thin-film transistor was fabricated with Dispersion A2 obtained in Example 2. With respect to that transistor, the drain voltage and drain current were measured at different gate voltages, respectively. As pronounced saturation regions were observed on the drain current-drain voltage curves, it was indicated that the transistor would be drivable as a field-effect transistor having typical n-type characteristics. The transistor was dried for 1 hour in a vacuum oven controlled at 40° C., and was then measured for transistor characteristics under high vacuum. The electron mobility and threshold voltage value calculated as transistor characteristic values from the drain current-drain voltage curves were $2.49 \times 10^{-6}$ cm$^2$/Vs and 3.9 V, respectively. The results are shown in Table 1.

TABLE 1

Characteristics of Organic Thin-film Transistors

| | Used dispersion | Heat treatment temperature (° C.) | Mobility μ (cm$^2$/Vs) | Threshold voltage value (V) | ON/OFF ratio |
|---|---|---|---|---|---|
| Example 5 | A1 | 50 | $10.7 \times 10^{-6}$ | 32 | 100 |
| Example 6 | A2 | 40 | $2.49 \times 10^{-6}$ | 3.9 | 100 |

Examples 7 to 10

Similar to Example 5, organic thin-film transistors were fabricated with a dispersion prepared before use by subjecting Dispersion A3, which had been obtained in Example 3, to ultrasonication. With respect to each transistor so obtained, the drain voltage and drain current were measured at different gate voltages, respectively. As pronounced saturation regions were observed on the drain current-drain voltage curves, it was indicated that the transistor would be drivable as a field-effect transistor having typical n-type characteristics. The transistor was dried for 1 hour in a vacuum oven controlled at 40° C., and was then measured for transistor characteristics under high vacuum. Subsequently, the transistor was subjected to further heat treatment at a set temperature (100 to 160° C.) for 10 hours in a vacuum oven. Its transistor characteristics were measured again. Its heat treatment temperature and transistor characteristic values as calculated from its drain current-drain voltage curves are shown in Table 2.

TABLE 2

Characteristics of Organic Thin-film Transistors

| | Used dispersion | Heat treatment temperature (° C.) | Mobility μ (cm$^2$/Vs) | Threshold voltage value (V) | ON/OFF ratio |
|---|---|---|---|---|---|
| Example 7 | A3 | 100 | $0.57 \times 10^{-6}$ | 62 | ≤10 |
| Example 8 | A3 | 120 | $3.26 \times 10^{-6}$ | 57 | 33 |
| Example 9 | A3 | 140 | $5.50 \times 10^{-6}$ | 53 | 47 |
| Example 10 | A3 | 160 | $4.28 \times 10^{-6}$ | 52 | 140 |

Example 11

A silicon substrate, which had on a surface thereof a silicon oxide film (thickness: 200 nm) to be used as a gate insulating layer, was provided. Using a shadow mask, a pattern of gold electrodes (100 nm) was formed as source/drain electrodes. At that time, the channel length and channel width were 10 μm and 1,000 μm, respectively. Subsequently, Dispersion A3 was cast as much as 2 μL by a pipette on the substrate to form a thin organic semiconductor film on the silicon substrate, followed by drying at 40° C. for 1 hour in vacuum.

As pronounced saturation regions were observed on the drain current-drain voltage curves, it was indicated that the thus-fabricated transistor would be drivable as a field-effect transistor having typical n-type characteristics. The electron mobility and threshold voltage value calculated as transistor characteristic values from the drain current-drain voltage curves were $3.3 \times 10^{-5}$ cm$^2$/Vs and 38 V, respectively.

Example 12

The organic thin-film transistor fabricated in Example 11 was subjected to heat treatment at 180° C. for 10 hours in a vacuum oven to obtain an organic thin-film transistor of Example 11.

As pronounced saturation regions were observed on the drain current-drain voltage curves, it was indicated that the transistor would be drivable as a field-effect transistor having typical n-type characteristics. The electron mobility and threshold voltage value calculated as transistor characteristic values from the drain current-drain voltage curves were $1.8 \times 10^{-4}$ cm$^2$/Vs and 64 V, respectively.

Example 13

A silicon substrate, which had on a surface thereof a silicon oxide film (thickness: 200 nm) to be used as a gate insulating layer, was provided. Using a shadow mask, a pattern of gold electrodes (100 nm) was formed as source/drain electrodes. At that time, the channel length and channel width were 10 μm and 1,000 μm, respectively. After the substrate was washed, a toluene solution with ODTS (octadecyl trichlorosilane) contained therein was dropped onto the substrate, followed by treatment at 40° C. for 10 minutes. The substrate was washed again. Subsequently, Dispersion A4 was cast as much as 5 μL by a pipette on the substrate, followed by drying in vacuum (40° C.) to form a thin organic semiconductor film on the silicon substrate.

As pronounced saturation regions were observed on the drain current-drain voltage curves, it was indicated that the thus-fabricated transistor would be drivable as a field-effect transistor having typical n-type characteristics. The electron mobility, threshold voltage value and ON/OFF ratio calculated as transistor characteristic values from the drain current-drain voltage curves were $1.1 \times 10^{-3}$ cm$^2$/Vs, 47 V and $10^3$, respectively.

Example 14

The device fabricated in Example 13 was subjected to heat treatment at 180° C. under a high-purity nitrogen atmosphere. Upon observation of the thin organic semiconductor film of the thus-obtained device under AFM (atomic force microscope), it was confirmed that owing to the heat treatment conducted as described above, the surface was smoothened into a uniform film.

As pronounced saturation regions were observed on the drain current-drain voltage curves, it was indicated that the thus-fabricated transistor would be drivable as a field-effect transistor having typical n-type characteristics. The electron mobility, threshold voltage value and ON/OFF ratio calculated as transistor characteristic values from the drain current-drain voltage curves were $2.7 \times 10^{-2}$ cm$^2$/Vs, 50 V and $10^5$, respectively.

INDUSTRIAL APPLICABILITY

According to the present invention, organic semiconductor materials can be provided. These organic semiconductor materials have high electron mobility and high ON/OFF values, and make it possible to form thin organic semiconductor films by a coating process or printing process that uses the fine-particulate organic semiconductor materials. In addition, the present invention can also provide organic thin-film transistors fabricated by using the organic semiconductor materials.

LEGEND

11 Insulating layer
12 Source electrode
13 Drain electrode
14 Gate electrode
15 Thin organic semiconductor film
16 Substrate

The invention claimed is:

1. A dispersion for forming an organic semiconductor film, which is useful in forming the organic semiconductor film, the dispersion comprising:

an organic solvent comprising an aprotic polar solvent having a specific inductive capacity of from 30-60; and a fine-particulate organic semiconductor material dispersed in the organic solvent, wherein the fine-particulate organic semiconductor material is in a form of fine particles and is usable as an organic semiconductor material, the fine particles are fine thermotropic liquid crystal particles that undergo a phase transition into a liquid crystal state when heated to a temperature of from 50° C. to 350° C., and the fine particles comprise a perylene tetracarboxylic diimide derivative, wherein the perylene tetracarboxylic diimide derivative is N,N'-ditridecyl perylene tetracarboxylic diimide represented by the following structural formula (1):

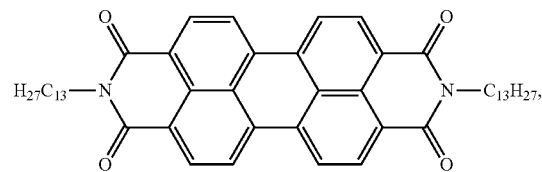

or N,N'-bis(3-(n-dodecyloxy)-n-propyl)-3,4,9,10-perylene tetracarboxylic diimide represented by the following structural formula (2):

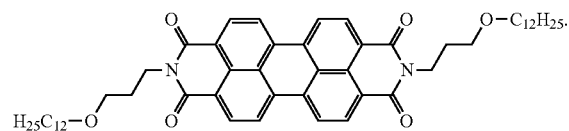

2. A process for producing a thin organic semiconductor film, which comprises coating and drying the dispersion according to claim 1 on a substrate, and then subjecting a resultant coating film to heat treatment at a temperature of from 50° C. to 350° C. such that the fine-particulate organic semiconductor material in the film are allowed to undergo a phase transition into a liquid crystal state to form a uniform thin organic semiconductor film on the substrate.

3. An organic thin-film transistor provided with a substrate and at least a gate electrode, gate insulating layer, thin organic semiconductor film, source electrode and drain electrode formed on the substrate, wherein the thin organic semiconductor film is formed by the process according to claim 2.

4. The dispersion according to claim 1, wherein the phase transition into the liquid crystal state takes place at a temperature of from 100° C. to 250° C.

5. The dispersion according to claim 1, wherein the fine particles have an average particle size of from 10 nm to 10 µm.

* * * * *